US 6,610,273 B2
(12) United States Patent
Wu et al.

(10) Patent No.: US 6,610,273 B2
(45) Date of Patent: Aug. 26, 2003

(54) PROCESS FOR MAKING CHEMICALLY STABLE C-17/21 OH 20-KETOSTEROID AEROSOL PRODUCTS

(75) Inventors: Zheng Z. Wu, Woodbury, MN (US); Nayna Govind, West Bridgford (GB); Peter R. Johnson, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/970,746

(22) Filed: Oct. 4, 2001

(65) Prior Publication Data

US 2002/0071810 A1 Jun. 13, 2002

Related U.S. Application Data

(62) Division of application No. 09/592,885, filed on Jun. 13, 2000, now Pat. No. 6,315,985.
(60) Provisional application No. 60/139,961, filed on Jun. 18, 1999.

(51) Int. Cl.[7] .............................. A61K 9/12; A61K 9/14
(52) U.S. Cl. ............................ 424/45; 424/46; 424/489
(58) Field of Search .............................. 424/45, 46, 489

(56) References Cited

U.S. PATENT DOCUMENTS

| | | |
|---|---|---|
| 5,743,251 A | 4/1998 | Howell et al. |
| 5,766,573 A | 6/1998 | Purewal |
| 5,776,432 A | 7/1998 | Schultz et al. |
| 5,776,433 A | 7/1998 | Tzou et al. |
| 5,891,420 A | 4/1999 | Cutie |
| 6,006,745 A | 12/1999 | Marecki |
| 6,039,932 A | 3/2000 | Govind et al. |
| 6,143,277 A | 11/2000 | Ashurst et al. |
| 6,149,892 A | 11/2000 | Britto |
| 6,315,985 B1 | 11/2001 | Wu |

FOREIGN PATENT DOCUMENTS

| | | |
|---|---|---|
| CA | 2130867 | 2/1995 |
| EP | 0338670 | 10/1989 |
| EP | 0642992 | 3/1995 |
| WO | 96/32099 | 10/1996 |
| WO | 96/32150 | 10/1996 |
| WO | 96/32151 | 10/1996 |
| WO | 96/32345 | 10/1996 |
| WO | 96/40042 | 12/1996 |
| WO | 98/13031 | 4/1998 |
| WO | 98/24420 | 6/1998 |
| WO | 98/52542 | 11/1998 |
| WO | 99/47195 | 9/1999 |
| WO | WO 00/30608 | 6/2000 |
| WO | 00/30608 | 6/2000 |

OTHER PUBLICATIONS

"New SilcoCan Canister with Pressure/Vacuum Guage", *Restek Advantage Chromatography Newsletter*, online at URL:http://www.restekcorp.com/advantage/e96seven.htm, 1996.
Lee, et al, "New Steroidal Anti–Inflammatory Drugs", *New Developments in Antirheumatic Therapy, Inflammation and Drug Therapy Series*, Chapter 6, vol. III, pp. 153–169, (Kluwer Academic Publishers, 1989).
George, R.F., *Wilson and Grisvold's Textbook of Organic Medicinal and Pharmaceutical Chemistry*, 8th Edition, p 703, table 18–13 (J.B. Lippincott Co., Philadelphia, 1982).

Primary Examiner—Michael G. Hartley
Assistant Examiner—M. Haghighatian
(74) Attorney, Agent, or Firm—Ted Ringsred; Bob Sprague

(57) ABSTRACT

A medicinal aerosol steroid solution formulation product with enhanced chemical stability. The steroid is a 20-ketosteroid having an OH group at the C-17 or C-21 position and the aerosol container has a non-metal interior surface which has been found to reduce chemical degradation of such steroids.

17 Claims, 5 Drawing Sheets

Graph A. Total Impurity Levels of Budesonide (0.22%) in Solution Formulations (HFA-134a/Ethanol 11%) In Three Different Containers, Incubated at 40°C/75%RH

PROCESS FOR MAKING CHEMICALLY STABLE C-17/21 OH 20-KETOSTEROID AEROSOL PRODUCTS

RELATED APPLICATIONS

This application is a divisional of application Ser. No. 09/592,885, filed on Jun. 13, 2000 now U.S. Pat. No. 6,315,985, and claims the benefit of earlier filed provisional application No. 60/139,961, filed on Jun. 18, 1999, (now abandon).

FIELD

The present invention relates to medicinal aerosol products and, in particular, to aerosol products such as metered dose inhalers for delivery of steroids. The invention is particularly related to certain 20-ketosteroids that have been found to be highly susceptible to chemical degradation when formulated as solution aerosol products, and provides a way of enhancing chemical stability of such steroids.

BACKGROUND

Structure I shown below is a typical core structure for a large number of natural and synthetic 20-ketosteroids, with the standard IUPAC numbering system of the carbon positions 1 to 21 indicated.

I

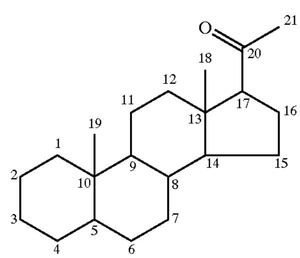

These types of steroids, with varying substituents and bonding, have many well-known therapeutic uses, especially based upon their anti-inflammatory activity. It is often desirable to deliver such steroids topically using aerosol spray devices, such as metered dose inhalers (MDIs). MDIs are commonly used to deliver steroids, e.g., beclomethasone dipropionate, to the airways of patients via oral or nasal inhalation for the treatment of asthma and allergic rhinitis.

One common difficulty, however, in making products for delivering steroids has been that they are often chemically unstable in aerosol formulations and degrade during storage. A great deal of research has been directed at steroid degradation. Chemical degradation is especially problematic when the steroid is dissolved in the formulation and, consequently, the vast majority of marketed MDI steroid products are formulated as particulate suspensions of the steroid, which are much less susceptible to chemical degradation than solutions. For example, it is believed that all currently marketed CFC-containing MDI products for delivering steroids are available only as particulate suspension formulations in CFC propellants.

More recently, some selected steroids have been reformulated as solutions in non-CFC hydrofluorocarbon (HFC) propellants with ethanol. In the case of beclomethasone dipropionate, for example, solution formulations are disclosed in U.S. Pat. No. 5,766,573 which are surprisingly chemically stable in propellant HFC 134a and/or 227 and ethanol in a conventional aluminum canister. Likewise, ciclesonide formulations are surprisingly chemically stable in certain solution MDI formulations disclosed in WO98/52542. Solution formulations of flunisolide are disclosed in U.S. Pat. No. 5,776,433, where it is indicated that chemical stability may be enhanced by using additives like water, sorbitan trioleate, and cetylpyridinium chloride, and also that certain containers such as glass and resin coated aluminum enhance chemical stability and/or minimize the absorption of flunisolide onto the container wall. Also, WO96/40042 discloses that aqueous formulations of triamcinolone acetonide in neutral or basic solutions undergo oxidative degradation catalyzed by trace levels of metal ions, especially copper, and proposes the use of EDTA as sequestering agent and/or adjusting pH.

Despite these limited examples, though, most commercial MDI formulations of steroids and other drugs have continued to be particulate suspensions. WO98/13031, for example, discloses recent work on reformulating budesonide as a non-CFC suspension formulation. However, suspension formulations of a medicament are more likely to encounter problems with physical instability (e.g., agglomeration, crystal growth and deposition on the container wall, all resulting in inconsistent dosage delivery).

A drug delivery device providing medicinal steroid solution formulations with enhanced chemical stability would offer some significant advantages over suspension formulations. Besides homogeneity, solution formulations have been found in some cases—e.g., using HFC propellants and low ethanol content—to give dramatically higher respirable fractions (i.e., the percentage of active ingredient able to reach the airways of the lung) compared to a particulate suspension of the steroid drug. See U.S. Pat. No. 5,776,432. Furthermore, an aerosol product providing a chemically and physically stable aerosol steroid formulation using non-CFC propellant would offer the advantage of being more ozone friendly than currently available aerosol products with CFCs.

Nevertheless, despite a substantial need, the problem of chemical degradation in steroid solution aerosol products has been poorly understood. Until now there has been no way to identify which steroids are likely to be most stable as solution aerosols and which will be most sensitive to degradation in solution aerosol products or how to reduce such degradation.

SUMMARY

It has now been found that those steroids in particular having a C-20 ketone and an OH group at the C-17 position or, especially, the C-21 position or both (hereafter collectively referred to as "C-17/21 OH 20-ketosteroids") are subject to enhanced chemical degradation when stored in contact with a metal container (particularly the metal oxide e.g., $Al_2O_3$ layer that forms on the interior surface of the container). Moreover, the vast majority of MDI's on the market, including all MDI steroid products, use aerosol containers made of metal, usually aluminum. By utilizing an aerosol container having a non-metal interior surface it is possible to produce solution aerosol formulations of C-17/21 OH 20-ketosteroids having enhanced chemical stability.

Generic structures for typical C-17 OH, C-21 OH, and C-17 and 21 OH 20-ketosteroids are shown below in structures II–IV, respectively.

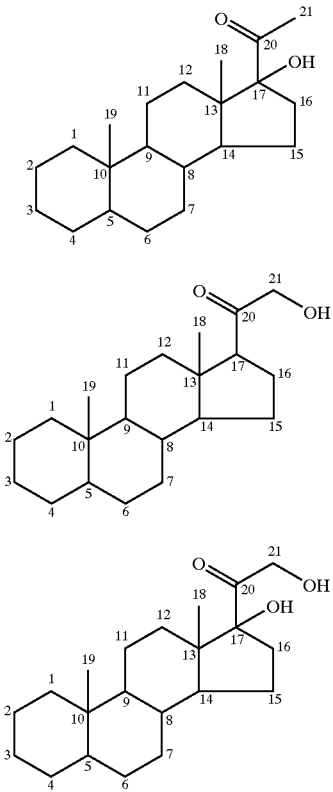

The present invention is especially preferred with respect to C-21 OH 20-ketosteroids (with or without a C-17 OH group). The C-21 OH group can substantially increase biological activity of a steroid, but such steroids are also much more susceptible to chemical degradation in the presence of metal. Particularly preferred 20-ketosteroids are budesonide, triamcinolone acetonide, dexamethasone, and betamethasone 17-valerate, all of which have an OH group at the C-21 position. These steroids are all currently on the market as CFC particulate suspension formulations in metered dose inhalers and, at least in the case of budesonide, work has been conducted to reformulate this important steroid as a non-CFC suspension product in HFA propellants. See PCT published application WO98/13031.

The most preferred type of container for use in the present invention is a conventional aluminum (or aluminum alloy) aerosol canister, but with an interior coating of an inert material, such as a spray-coated, baked epoxy-phenolic lacquer (available from Cebal Printal U.K. Ltd.). Other metals, such as stainless steel, may likewise be used with an inert interior coating. It is also preferred that the internal surfaces of metal valve components in contact with the formulation are similarly coated with an inert material. Another preferred coating for the inside of the container is perfluoroethylenepropylene (FEP).

A preferred coating for the metal valve components is a very thin layer of glass, or other material, deposited by gas vapor deposition. Such coating is preferably used on all of the metal valve components in contact with the formulation, including the inside and outside of the metering chamber, inside and outside of the bottle emptier (if any), and the inside and outside of the valve stem (if metal), and may also be used to coat the inside of the canister. The preferred such coating technique is the Silcosteel™ process available from Restek Corporation, Bellefonte, Pa. The Silcosteel™ aspect of the invention is useful even outside the context of the chemical degradation problem, for both solution and suspension formulations.

Preferred formulations use a liquified propellant such as hydrogen-containing (non-CFC) propellants, more preferably hydrofluorocarbons, such as 134a and/or 227. Particularly preferred formulations include about 0.1 to 0.5% C-17/21 OH 20-ketosteroid about 75 to 99% 134a and/or 227, and about 1 to 25% w/w ethanol, more preferably about 80 to 95% 134a and/or 227, and about 5 to 20% ethanol. The most preferred medicinal aerosol products according to the invention are MDI's comprising about 0.1 to 0.5% budesonide or triamcinolone acetonide dissolved in about 80–95% 134a and/or 227 and about 5–20% ethanol, contained in a coated aluminum aerosol canister equipped with a metering valve.

It should also be noted that chemical stability is especially critical for MDIs since these medicinal aerosol products must remain stable and deliver accurate dosing throughout their shelf life (typically 2 to 3 years) and in use. Only a very small amount of chemical degradation can be tolerated. Moreover, by providing chemically stable solutions of C-17/21 OH 20-ketosteroids, such as budesonide, triamcinolone acetonide, dexamethasone, and betamethasone 17-valerate, MDIs can be made that produce extra-fine aerosols resulting in higher respirable fractions than suspension formulation products.

It can thus be seen that the present invention provides a medicinal aerosol steroid solution formulation product with enhanced chemical stability. Such product includes a container equipped with a dispensing valve and containing a medicinal aerosol formulation having a 20-ketosteroid drug dissolved therein. The 20-ketosteroid is other than flunisolide and has an OH group at the C-17 or C-21 position or both, and the container is provided with a non-metal interior surface so as to reduce chemical degradation.

Also provided is a method of reducing the chemical degradation of a medicinal 20-ketosteroid dissolved in a formulation contained in a metal container, said 20-ketosteroid being other than flunisolide and having an OH group at the C-17 position or C-21 position or both, comprising the step of providing a coating of inert material on the interior surface of the metal container so as to reduce reaction of the 20-ketosteroid with metal oxides from the container.

The invention further provides a process for making a chemically stable 20-ketosteroid solution aerosol product, by filling into a container an aerosol formulation comprising a dissolved 20-ketosteroid other than flunisolide, said 20-ketosteroid having an OH group at the C-17 position or C-21 position or both, and said container having an inert non-metal interior surface so as to avoid chemical degradation of the 20-ketosteroid due to interaction with the container.

BRIEF DESCRIPTION OF THE DRAWINGS

The invention will be described with reference to the following drawings, wherein.

DETAILED DESCRIPTION

Figure 1:
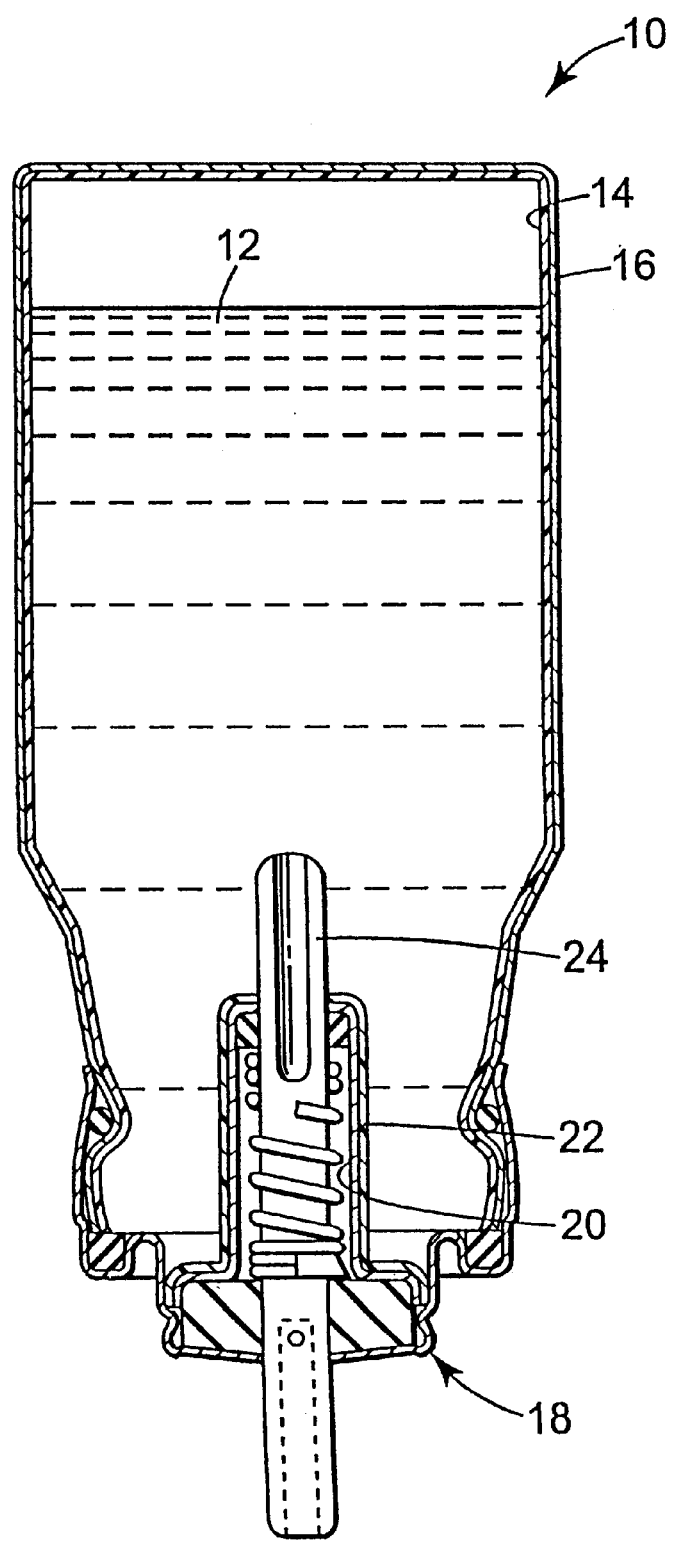
FIG. 1 is a cross-sectional view of a metered dose inhaler containing a medicinal 20-ketosteroid formulation with enhanced chemical stability according to the present invention.

Turning to FIG. 1, there is shown a medicinal aerosol device 10 comprising a pressurizable metal aerosol container 16 equipped with a metering valve 18. The metal container 16 is preferably made of aluminum (i.e. aluminum or aluminum alloy) and has an inert interior coating layer 14. The metering valve 18 includes a metal metering chamber 20 with a coating layer 22. Moreover, although not shown, it is preferred that as many other metal surfaces in contact with the formulation 12 as feasible are also coated with an inert layer (e.g., the interior of the metering chamber). It is also preferred to use a valve design that minimizes metal surfaces in contact with the formulation 12. For example, it is preferred in the context of the present invention to use a plastic valve stem 24 instead of metal.

Figure 2:
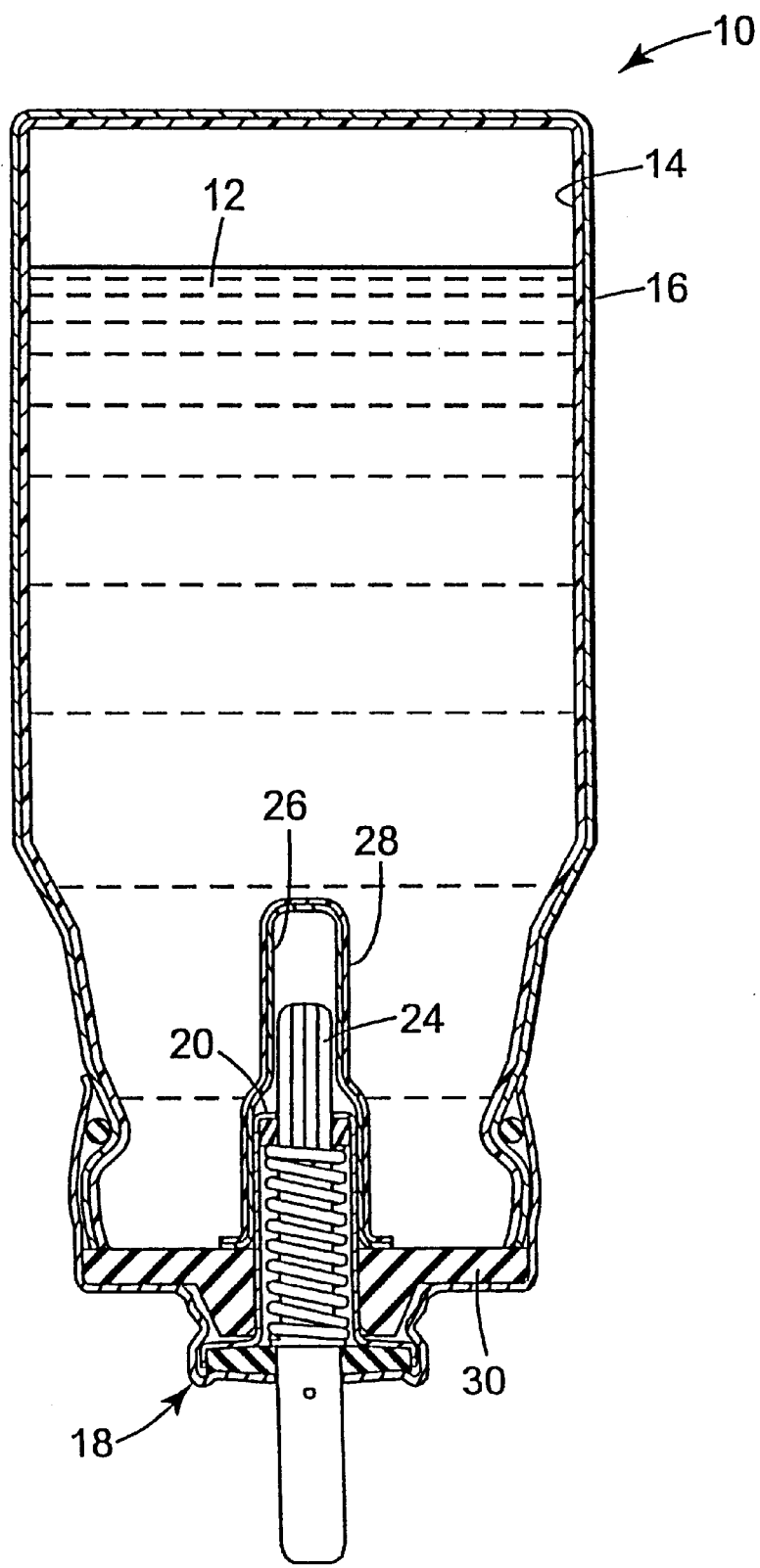
FIG. 2 is the same as FIG. 1, but with a modified valve configuration.

FIG. 2 shows an alternative preferred embodiment that is essentially the same as FIG. 1, but utilizes a fixed bottle emptier 26, with coating layer 28. Also, a solution gasket 30 is used to further prevent contact of the formulation with metal components.

The medicinal aerosol formulation 12 preferably includes a non-CFC propellant, a cosolvent (if necessary), and a therapeutically effective amount of dissolved C-17/21 OH 20-ketosteroid. A therapeutically effective amount will normally be a concentration so as to provide in the range of about 100 to 1500 mg per day using one to eight puffs. Preferred propellants include hydrogen containing propellants, such as HFCs 134a and/or 227. Ethanol is a preferred cosolvent, although other cosolvents and solubilization aids (e.g., surfactants) may be used. The amount of cosolvent used is preferably an amount sufficient to completely dissolve the 20-ketosteroid. The formulation 12 may also include other excipients, such as stabilizers, antioxidants, flavoring agents, and the like.

Although there are many possible C-17/21 OH 20-ketosteroids, there are two preferred types set forth below as structures V and VI:

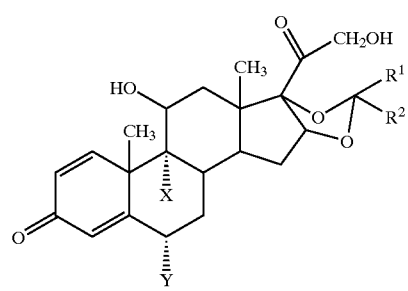

V

Wherein X is H, Cl, or F; Y is H, F, or Me; $R^1$ is H or an alkyl group; $R^2$ is an alkyl group; and provided that when Y is F, then X is not H. Preferred $R^1$ and/or $R^2$ alkyl groups are methyl, ethyl, propyl, butyl, pentyl, and hexyl groups, including their branched and cyclic isomers. $R^1$ may form a ring with $R^2$, preferably a cyclopentyl or cyclohexyl ring.

Examples of known 20-ketosteroids according to structure V include budesonide, triamcinolone acetonide, desonide, and fluocinolone acetonide.

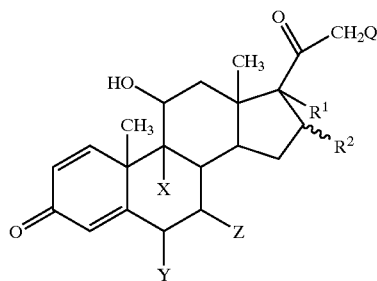

Wherein Q is OH, H, Cl, or $PO(ONa)_2$; X is H, Cl, or F; Y is H, F, or Me;. Z is H or Cl; $R^1$ is H, OH or propionate provided that when Q is not OH, then $R^1$ must be OH; and $R^2$ is H, OH, or Me.

Examples of known 20-ketosteroids according to structure VI include alclometasone, beclomethasone, beclomethasone 17-monopropionate, betamethasone, betamethasone 17-valerate, clocortolone, desoximetasone, dexamethasone, dexamethasone sodium phosphate, dexamethasone 21-isonicotinate, diflorasone, flumethasone, methylprednisolone, paramethasone, prednisolone, tramcinolone, clobetasol, and fluorometholone.

Within the group of C-17/21 OH 20-ketosteroids, those having an OH group at C-21, with or without an OH group at C-17, suffer from more severe degradation in the presence of metal oxide than 20-ketosteroids having an OH group at C-17, but not at C-21. For example, beclomethasone 17-monopropionate (17-BMP, 21-OH) degrades in ethanol/ $Al_2O_3$ about 100 times faster than its isomer 21-BMP (17-OH). This is important since it has been reported that the Structure-Activity Relationship for a C-21 OH group has an enhancement factor toward anti-inflammatory activity of 25 compared to an enhancement factor of only 4 for a C-17 OH group. See Doerge, R. F., *Wilson and Grisvold's Textbook of Organic Medicinal and Pharmaceutical Chemistry*, $8^{th}$ Edition, p. 703, table 18-13 (J. B. Lippincott Co., Philidelphia, 1982).

For particular structural examples, four preferred C-17/21 OH 20-ketosteroids according to the present invention, budesonide, triamcinolone acetonide, betamethasone 17-valerate, and dexamethasone, have the following structures:

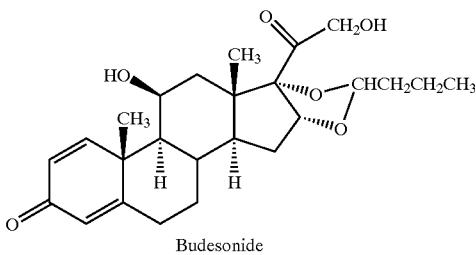

Budesonide

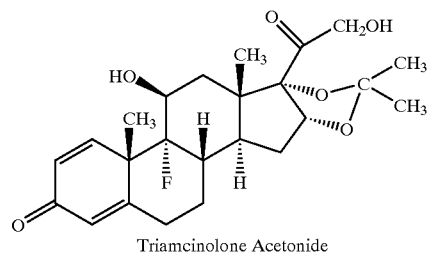

Triamcinolone Acetonide

-continued
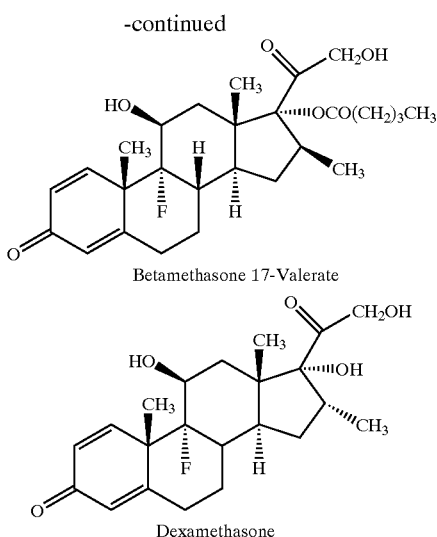
Betamethasone 17-Valerate
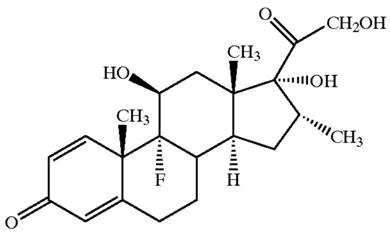
Dexamethasone

The C-17/21 OH 20-ketosteroid is dissolved in the aerosol formulation and preferably contained in an inertly coated metal container. As used herein, the terms "coated", "inert coating" and the like simply refer to a non-metal interior coating that does not promote degradation at the OH substituents on C-17/21 OH 20-ketosteroids. Inert coating materials include any suitable polymer, lacquer, resin, or other coating treatment that creates a barrier to chemical interaction of the dissolved C-17/21 OH 20-ketosteroid and metal on the container (especially metal oxides).

Examples of suitable interior coatings include epoxy-phenolic resins, epoxy-urea-formaldehyde resins, polytetrafluroethylene (PTFE), perfluoroethylenepropylene (FEP), perfluoroalkoxyalkane (PFA), ethylene tetrafluoroethylene (ETFE), poly(vinyldiene fluoride) (PVDF), and chlorinated ethylene tetrafluoroethylene. Blends may be used of fluorinated polymers with non-fluorinated polymers such as polyamides, polyimides, polyethersulfones, polyphenylene sulfides, and amine-formaldehyde thermosetting resins. Specific blends include PTFE/FEP/polyamideimide, PTFE/polyether sulphone (PES) and FEP-benzoguanamine. Preferred interior coating materials are epoxy-phenolic resins, epoxy-urea-formaldehyde resins, PTFE, and FEP. Additional information regarding interior can coatings is taught in, e.g., EP 642992, WO96/32099, WO 96/32150, WO96/32151, and WO96/32345, which disclose interior can coatings for drug suspension formulation products.

A preferred coating for the metal valve components is a very thin layer of fused silica glass, or other material, deposited by gas vapor deposition. Such coating is preferably used on all of the metal valve components in contact with the formulation, including the inside and outside of the metering chamber, inside and outside of the bottle emptier (if any), and the inside and outside of the valve stem (if metal). The preferred such coating technique is the Silcosteel™ process available from Restek Corporation, Bellefonte, Pa. This process deposits a submicron layer of fused silica glass on the metal components and can be used both on the valve components and on the interior of the canister. Not only is it helpful in preventing chemical reaction with the metal, but passivation of the metal surface using the Silcosteel process can provide a smooth surface on, for example, the valve stem so as to reduce friction and help prevent valve clogging, and can also reduce oxidation of the metal that can introduce particulate material into the system. The Silcosteel™ aspect of the invention is thus useful even outside the context of the chemical degradation problem, for both solution and suspension formulations. The Silcosteel process is performed at a temperature of 400° C., which has the added benefit of thermally removing residual oils on the metal surface.

It is also possible to use containers made from non-metal materials, such as glass or plastic (e.g., polyethylene terephthalate, from Precise Plastic Ltd., U.K.). In the case of glass containers, however, it is preferred to use glass having a low metal oxide content. According to the American Society for Testing and Materials (ASTM), Type I/Class A glass contains 2% aluminum oxide, whereas Type II/Class B glass contains 7% aluminum oxide. The former is therefore preferred. Type III (soda-lime) glass vials may also be used (available from Wheaton Coated Products). High metal oxide content glass should also be avoided during development and testing of formulations containing C-17 and/or C-21 OH 20-ketosteroids because such use could cause unsuspected chemical degradation due to the glass metal oxide content.

Coated containers can be made by pre-coating the metal roll stock before forming the container or by coating the container after it is made, by various techniques known in the art of coating. For example, suitable coating procedures include plasma coating, electrostatic dry powder coating, impregnating/spraying, hard anodization with polymer deposition, chemical vapor deposition (CVD), physical vapor deposition (PVD), as well as other procedures known in the art for this purpose. Preferably, the containers are coated with an epoxy resin and then baked. Suitable coated containers can be obtained from, for example, Cebal Printal U.K. Ltd.

Preferred products/devices according to the present invention are pressurized aerosols such as MDIs that use liquefied gas propellants, including chlorofluorocarbons (CFCs), hydrofluorocarbons (HFCs), fluorocarbons (FCs), hydrocarbons (HCs), hydrochlorofluorocarbons (HCFCs), and dimethyl ether (DME). Propellants containing hydrogen are preferred. Ethanol may also be included to assist in solubilizing the 20-ketosteroid, preferably in an amount of about 1–25%. Formulations comprising dissolved C-17/21 OH 20-ketosteroid, HFC propellant, such as 134a and/or 227, with 5–20% ethanol are particularly preferred. Also, it is generally preferred that the formulations are essentially non-aqueous, meaning that they do not include added water, although very small amounts of water may be present due to water ingress and/or as a residual in formulation components (such as ethanol). Formulations will preferably have less than about 3%, and more preferably less than about 0.5% water content.

The containers can be equipped with any suitable conventional or unconventional dispensing valve, preferably a metered dose valve.

The following examples illustrate various aspects of the invention.

EXAMPLE 1

The following illustrates the effect of a metal oxide ($Al_2O_3$) in the degradation of a C-17/21 OH 20-ketosteroid, in this case budesonide, which has an OH group attached on the C-21 carbon position.

At ambient temperature, a 3 mL ethanol solution of budesonide (0.007 M) was mixed with 0.1 g of aluminum oxide (Aldrich, neutral, activated Brockmann I, 150 mesh), which mimics aluminum oxide existing on the inner surface of aluminum containers. The mixture was held at 75° C. for several days, and an aliquot was taken at each of the time intervals given in the Table 1. Each aliquot was filtered with a syringe filter and diluted with acetonitrile by 20 times for HPLC analysis to determine the recovery of budesonide with respect to the initial concentration. The recoveries of budesonide were compared with a reference, which contained the same concentration of budesonide but in ethanol solution without aluminum oxide. The results are summarized in Table 1.

TABLE 1

Recovery (%) of budesonide in a mixture of ethanol/aluminum oxide at 75° C. or in ethanol at 75° C.

| Time (Hours) | In Ethanol/Aluminum Oxide | In Ethanol |
| --- | --- | --- |
| 0 | 100 | 100 |
| 6 | 4.97 | — |
| 24 | 0.20 | 99.2 |
| 48 | 0.22 | 99.4 |
| 168 | — | 95.5 |

In the presence of aluminum oxide, budesonide was almost totally consumed in 6 hours at 75° C. In contrast, without aluminum oxide the recovery of budesonide was as high as 95.5% in 168 hours at the same temperature. The data demonstrate that the presence of aluminum oxide substantially facilitates the decomposition of budesonide. Ethanol, however, appears to play only a minor role in the decomposition.

EXAMPLE 2

The following Example illustrates the effect of aluminum oxide in the degradation of another C-17/21 OH 20-ketosteroid, in this case triamcinolone acetonide, which has an OH attached to the C-21 carbon position.

At ambient temperature, a 3 mL ethanol solution of triamcinolone acetonide (0.007 M) was mixed with 0.1 g of aluminum oxide (Aldrich, neutral, activated Brockmann I, 150 mesh), which mimics aluminum oxide existing on the inner surface of aluminum containers. The mixture was held at 75° C. for several days, and an aliquot was taken at each of the time intervals given in the Table 2. Each aliquot was filtered with a syringe filter and diluted with acetonitrile by 20 times for HPLC analysis to determine the recovery of triamcinolone acetonide with respect to the initial concentration. The recoveries of triamcinolone acetonide were compared with a reference, which contained the same concentration of triamcinolone acetonide but in ethanol solution without aluminum oxide. The results are summarized in Table 2.

TABLE 2

Recovery (%) of triamcinolone acetonide in a mixture of ethanol/ aluminum oxide at 75° C. or in ethanol at 75° C.

| Time (Hours) | In Ethanol/Aluminum Oxide | In Ethanol |
| --- | --- | --- |
| 0 | 100 | 100 |
| 6 | 70.2 | — |
| 24 | 19.6 | 98.6 |
| 48 | 12.4 | 98.5 |
| 168 | — | 97.5 |

In the presence of aluminum oxide, triamcinolone acetonide recovery was 12.4% in 48 hours at 75° C. In contrast, without aluminum oxide the recovery of triamci-nolone acetonide was as high as 97.5% in 168 hours at the same temperature. The data demonstrate that the presence of aluminum oxide substantially facilitates the decomposition of triamcinolone acetonide. Ethanol, however, appears to play only a minor role in the decomposition.

EXAMPLE 3

The following Example illustrates the effect of aluminum oxide in the degradation of C-17/21 OH 20-ketosteroid, in the case dexamethasone, which has one OH attached to C-21 and another OH attached to C-17.

At ambient temperature, a 3 mL ethanol solution of dexamethasone (0.007 M) was mixed with 0.1 g of aluminum oxide (Aldrich, neutral, activated Brockmann I, 150 mesh), which mimics aluminum oxide existing on the inner surface of aluminum containers. The mixture was held at 75° C. for several hours, and an aliquot was taken at each of the time intervals given in Table 3. Each aliquote was filtered with a syringe filter and diluted with acetonitrile by 20 times for HPLC analysis to determine the recoveries of dexamethasone with respect to the inital concentration. The recoveries of dexamethasone were compared with a reference, which contained the same concentration of dexamethasone but in ethanol solution without aluminum oxide. The results are summmarized in following Table 3.

TABLE 3

Recovery (%) of dexamethasone in a mixture of ethanol/aluminum oxide at 75° C. or in ethanol at 75° C.

| Time (hours) | in Ethanol/Aluminum Oxide | in Ethanol |
| --- | --- | --- |
| 0 | 100 | 100 |
| 3 | 6.0 | — |
| 6 | 4.0 | — |
| 10 | 0.0 | — |
| 24 | — | 98.0 |
| 72 | — | 96.0 |
| 168 | — | 90.0 |

In the presence of aluminum oxide, dexamethasone completely degrades after ten hours at 75° C. In contrast, without aluminum oxide the recovery of dexamethasone is as high as 90% after 168 hours at the same temperature. The data demonstrate that aluminum oxide substantially facilitates degradation of dexamethasone in ethanol solution. Ethanol, however, appears to play a only a minor role in degradation.

EXAMPLE 4

Table 4 below shows results of solubility testing in mg/g of budesonide in P134a and P227 formulations at approximately 5° C.

TABLE 4

Solubility of budesonide

| | Budesonide Solubility mg/g (5° C.) | | |
| --- | --- | --- | --- |
| Sample | 1 | 2 | MEAN |
| P134a | 0.013 | 0.010 | 0.012 |
| P134a/5% EtOH | 0.459 | 0.471 | 0.465 |
| P134a/10% EtOH | 1.370 | 1.394 | 1.382 |
| P134a/15% EtOH | 2.686 | 2.711 | 2.699 |
| P134a/20% EtOH | 4.329 | 4.390 | 4.360 |
| P227 | 0.017 | 0.015 | 0.016 |
| P227/5% EtOH | 0.652 | 0.661 | 0.657 |

TABLE 4-continued

Solubility of budesonide

| Sample | Budesonide Solubility mg/g (5° C.) | | |
|---|---|---|---|
| | 1 | 2 | MEAN |
| P227/10% EtOH | 1.698 | 1.707 | 1.703 |
| P227/15% EtOH | 2.952 | 3.008 | 2.98 |
| P227/20% EtOH | 4.387 | 4.483 | 4.435 |

EXAMPLES 5–6

Experiments were conducted to test the influence of various factors on chemical stability of two exemplary budesonide solution formulations, examples 5 and 6, shown in Table 5.

TABLE 5

Exemplary budesonide formulations

| | % w/w |
|---|---|
| Example 5 | |
| Budesonide | 0.362 |
| Oleic acid | 0.029 |
| Ethanol absolute | 20.000 |
| Propellant 134a | 79.609 |
| Example 6 | |
| Budesonide | 0.327 |
| Oleic acid | 0.029 |
| Ethanol absolute | 20.000 |
| Propellant 227 | 79.644 |

The above formulations of Examples 5 and 6 were manufactured on a pilot-scale cold filler and filled into metered dose inhaler vials having various different components: different valve types, coated versus uncoated aluminum cans, and with and without a nylon desiccant insert. The units were then inverted and stored at either 40° C./85% RH for 14 days or 30° C./30% RH for 17 days prior to analysis of budesonide degradation.

The test results indicate that epoxy-phenolic lacquer-coated aluminum containers (from Cebal Printal U.K. Ltd.) showed in all but one case significantly enhanced chemical stability versus formulations in uncoated cans.

The type of valve used also had an impact on chemical stability. The greatest chemical stability enhancement was found in units using a Bespak 357 valve with EPDM seals, a Cebal epoxy lacquered can, and the formulation of Example 6. Nearly as stable were units equipped with a 3M Neotechnic Spraymiser™ HFA valve, a Cebal epoxy lacquered can, and the formulations of Examples 5 or 6. Also, none of the valves tested were coated and it is expected that this would further enhance chemical stability.

Other factors also appeared to affect chemical stability. Formulations using propellant 227 appeared to be slightly more stable. Containers having a desiccant generally exhibited reduced degradation compared to those without desiccant inserts. This suggests that water may increase degradation and that using dried ethanol may thus help further enhance chemical stability. Also, the use of certain antioxidants such as ascorbic acid and ascorbyl palmitate (but not vitamin E) appeared to enhance chemical stability, while the use of oleic acid appeared to reduce chemical stability.

EXAMPLE 7

Figure 3:
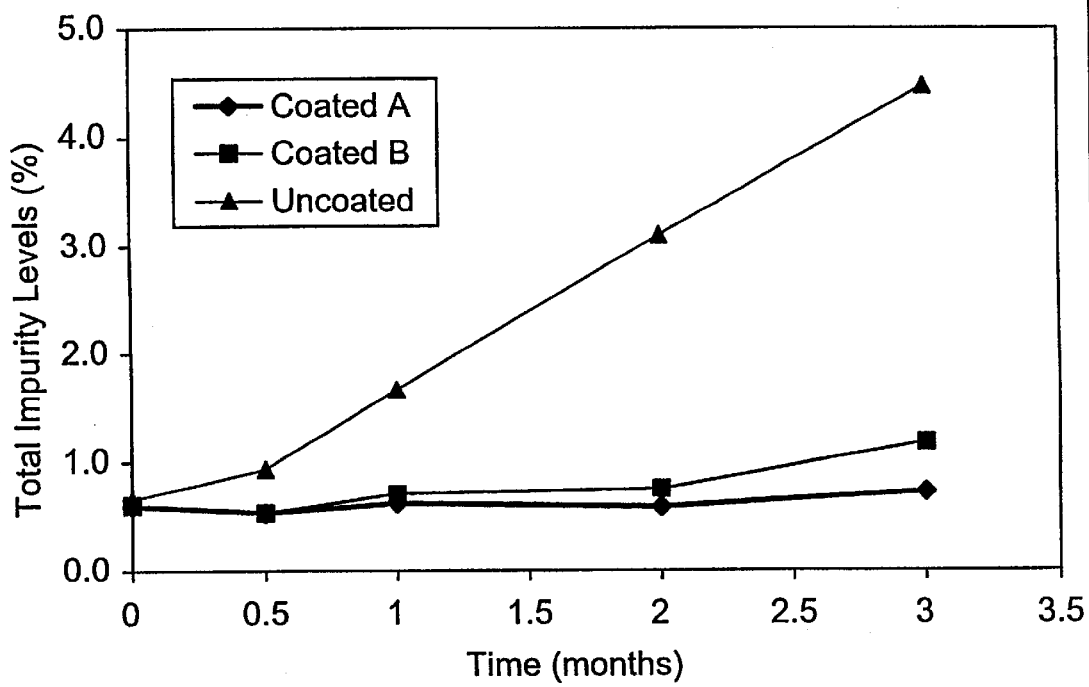
FIGS. 3–5 (Graphs A–C) show comparative impurity levels.

The following FIG. 3 (Graph A) shows comparative tests results on a budesonide solution formulation comprising 0.22% w/w budesonide, 11% w/w ethanol, and the remainder 134a. Three lots were stored at 40° C./75% RH. One lot (identified as "Coated A") was contained in aluminum cans coated with an epoxy-phenolic coating (Cebal Printal Ltd. U.K.) and capped with a blind ferrule and a continuous gasket (mad of DFDB 1085 elastomer, Union Carbide) so as to completely isolate the formulation from contact with metal surfaces. Another lot ("Coated B") was contained in the same type of cans as Coated A, but equipped with a functional valve ferrule (3M Neotechnic Spraymister™ solution valve) having a solution gasket to partially prevent contact of the formulation with the underside of the valve ferrule. A third lot ("Uncoated") was contained in uncoated aluminum cans equipped with the same valves as for Coated B.

It can be seen from Graph A that the formulation in the Uncoated containers underwent much greater chemical degradation compared to the two coated containers, and that the Coated A lot underwent the least amount of degradation.

EXAMPLES 8–9

Figure 4:
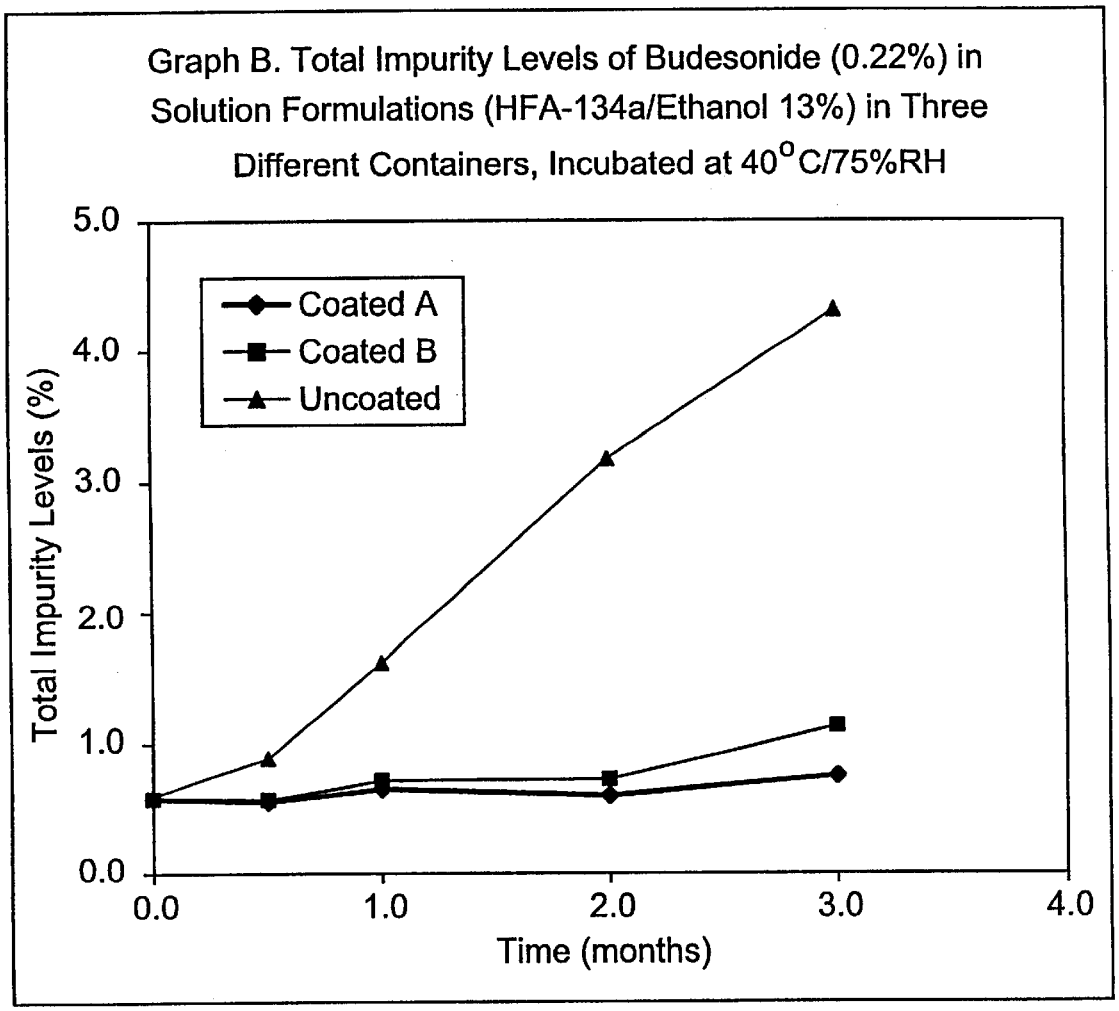
Figure 5:
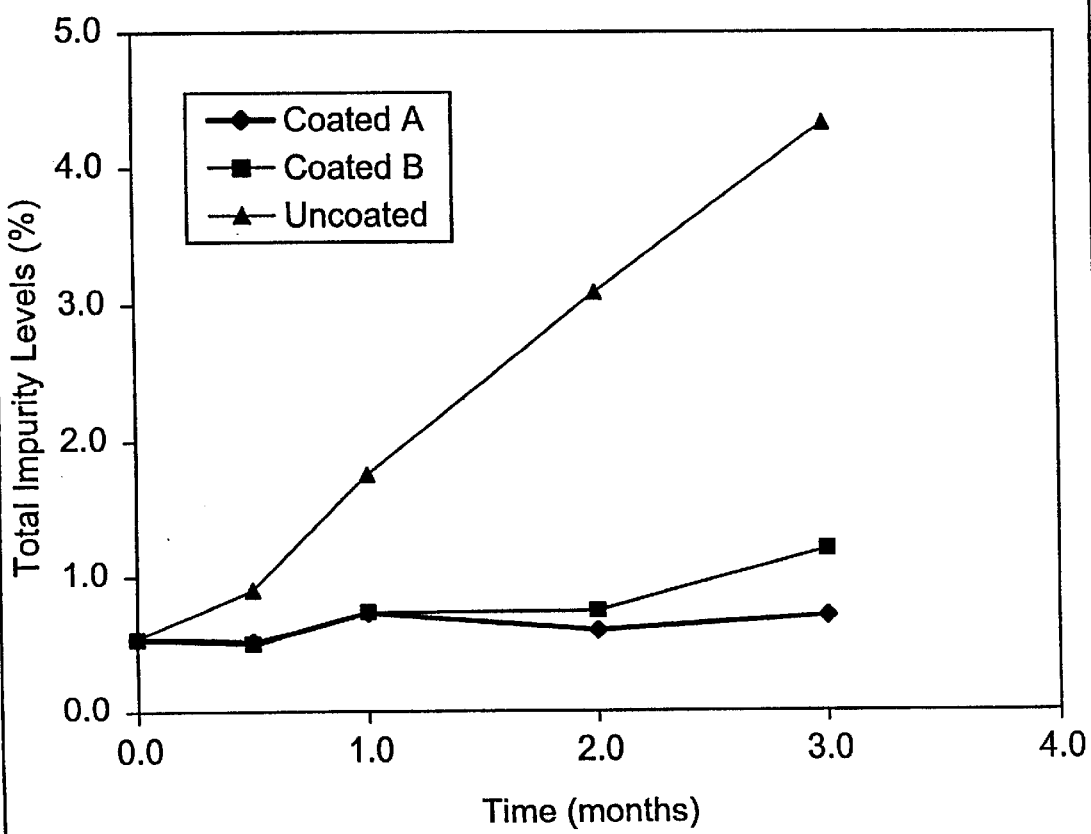

The same type of comparison (using the same kind of Coated A, Coated B, and Uncoated containers as in Example 7) was made for formulation Examples 8 and 9. In Example 8 the formulation contained 0.22% w/w budesonide dissolved in a mixture of 134a and 13% w/w ethanol. The Example 9 formulation had 0.17% w/w budesonide dissolved in 134a and 15% w/w ethanol. In both cases, shown in FIGS. 4 and 5 (Graphs B and C), respectively, the degradation rate was much greater in the Uncoated can, and degradation was least for Coated A.

EXAMPLE 10

Test was also conducted on solution formulations of about 0.2% w/w budesonide, 13% anhydrous ethanol, and 134a to determine the effect of different coating types on chemical stability. Two types of canister coatings were compared: phenolic epoxy coating (Cebal) Vs. an FEP coating (teflon-like polymer) from DuPont. Coated and uncoated valves similar to the design of FIG. 2 were compared: uncoated valves ("UV") vs. coated valves ("CV") with Restek's SilcoSteel coated parts. The interior and exterior surfaces of the valve stem, metering tank, and bottle emptier were made of stainless steel and were coated with a submicron layer of fused silica. The results are summarized in Tables 6 and 7 below.

TABLE 6

| Container Closure System | Initial Testing* Total Impurities % w/w | 1 month @40° C./75% RH Total Impurities % w/w |
|---|---|---|
| UV/Epoxy lot A | 1.09 | 0.98 |
| CV/FEP lot B | 1.17 | 1.36 |
| UV/FEP lot C | 1.36 | 2.31 |
| CV/Epoxy lot D | 1.17 | 0.95 |

TABLE 7

| Container Closure System | Initial Testing* % Degradation Compared to Standard | 1 month @40° C./75% RH % Degradation Compared to Standard |
|---|---|---|
| UV/Cebal lot A | 0.03 | 0.17 |
| CV/FEP lot B | 0.11 | 0.55 |

TABLE 7-continued

| Container Closure System | | Initial Testing* % Degradation Compared to Standard | 1 month @40° C./75% RH % Degradation Compared to Standard |
|---|---|---|---|
| FV/FEP | lot C | 0.30 | 1.50 |
| UV/Epoxy | lot D | 0.11 | 0.14 |

*Note: the units were made and stored at ambient for about 2 months before "initial" testing. They were then placed in 40° C./75% RH chamber for stability. Thus, the initials are actually about 2 months @ ambient and the 1 month @ 40° C./75% RH is in addition to that period.

The results in Tables 6 and 7 indicate (1) that the coated valves (CV) improve chemical stability, and (2) that the epoxy coated canisters result in lower impurities than the FEP coating. These differing results based on the coating type are interesting because the FEP coating should provide equal protection to the formulation and, since the extractables profile of the FEP is believed to be much cleaner than the epoxy canister, the FEP would have been expected to result in lower impurities.

However, the data indicates the epoxy can is superior to the FEP in preventing degradation. Without wishing to be held to any particular mechanism to explain the difference in results between the two coating types, it is hypothisized that it is not that the phenolic epoxy provides a better barrier, but rather that some adsorption of degradation products is taking place. Essentially, the phenolic epoxy may be "soaking up" the degradates. A small amount of budesonide may also be adsorbed too, but the amount is apparently too small to affect the target content amount.

The description and examples set forth above are intended to illustrate the invention, but are not intended to be limiting. To the contrary, it will be understood that the invention is intended to include all variations and modifications falling within the scope of the appended claims. Also, although the invention is specifically applicable to C-17/21 20-ketosteroids in solution, it will be understood that particular steroid structures may have variations that modify the IUPAC carbon position numbering, thereby resulting in a position number other than 17 and/or 21 for OH groups that are nonetheless at effectively the same relative location. For example, if one were to remove the C-19 carbon atom, the numbering would change such that C-21 would be renamed C-20. Such variations are intended to be within the scope of the invention and thus reference to "C-17" and "C-21" is intended herein to refer to the relative position based on the generic structures given above.

All percentages given herein are on a weight/weight (w/w) basis unless otherwise indicated. Also, all of the publications referred to herein are hereby incorporated by reference.

What is claimed is:

1. A method of reducing the chemical degradation of a medicinal 20-ketosteroid dissolved in an aerosol formulation including a hydrofluorocarbon propellant selected from the group consisting of 1,1,1,2-tetrafluoroethane, 1,1,1,2,3,3,3-heptafluoropropane, and mixtures thereof, contained in a metal container equipped with a metered dose dispensing valve, said dissolved 20-ketosteroid being other than flunisolide and having an OH group at the C-17 position or C-21 position or both, comprising the step of providing a non-metal oxide material on the interior surface of the metal container so as to reduce reaction of the 20-ketosteroid with metal oxides from the container.

2. A process for making a chemically stable steroid solution aerosol product by filling into a container equipped with a metered dose dispensing valve, an aerosol formulation including a hydrofluorocarbon propellant selected from the group consisting of 1,1,1,2-tetrafluoroethane, 1,1,1,2,3,3,3-heptafluoropropane, and mixtures thereof, and comprising a dissolved 20-ketosteroid other than flunisolide, said 20-ketosteroid having an OH group at the C-17 position or C-21 position or both, and said container having an inert non-metal oxide interior surface so as to avoid chemical degradation of the 20-ketosteroid due to interaction with metal oxides from the container.

3. The process of claim 2, wherein the container is made of aluminum having an inert interior coating.

4. The process of claim 3, wherein the interior coating is an epoxy-phenolic lacquer.

5. The process of claim 3, wherein the interior coating is a perfluoroethylenepropylene.

6. The process of claim 2, wherein the container is made of stainless steel with an interior coating of inert material.

7. The process of claim 2, wherein the medicinal aerosol formulation includes ethanol.

8. The process of claim 2, wherein the 20-ketosteroid has an OH group at the C-17 position, but not at the C-21 position.

9. The process of claim 2, wherein the 20-ketosteroid has an OH group at the C-21 position, but not at the C-17 position.

10. The process of claim 2, wherein the 20-ketosteroid has an OH group at both the C-17 and C-21 positions.

11. The process of claim 2, wherein the 20-ketosteroid is a corticosteroid selected from the group consisting of budesonide, triamcinolone acetonide, desonide, fluocinolone acetonide, alclometasone, beclomethasone, beclomethasone 17-monopropionate, betamethasone, betamethasone 17-valerate, clocortolone, desoximetasone, dexamethasone, dexamethasone sodium phosphate, dexamethasone 21-isonicotinate, diflorasone, flumethasone, methylprednisolone, paramethasone, prednisolone, triamcinolone, clobetasol, and fluorometholone.

12. The process of claim 2, wherein the 20-ketosteroid is budesonide.

13. The process of claim 2, wherein the 20-ketosteroid is triamcinolone acetonide.

14. The process of claim 2, wherein the 20-ketosteroid is dexamethasone.

15. The process of claim 2, wherein the 20-ketosteroid is betamethasone 17-valerate.

16. The process of claim 2 wherein the valve has a coating applied to it.

17. The process of claim 16, wherein metal valve components have a coating applied by vapor deposition.

* * * * *